(12) United States Patent
Chen et al.

(10) Patent No.: US 8,338,573 B2
(45) Date of Patent: Dec. 25, 2012

(54) CRYSTAL STRUCTURE OF CD147 EXTRACELLULAR REGION AND USE THEREOF

(75) Inventors: Zhinan Chen, Xi'an (CN); Ping Zhu, Xi'an (CN); Xiaoling Yu, Xi'an (CN); Bin Yang, Xi'an (CN); Xiangmin Yang, Xi'an (CN); Zheng Zhang, Xi'an (CN)

(73) Assignee: Zhinan Chen, Xi'an (CN)

( * ) Notice: Subject to any disclaimer, the term of this patent is extended or adjusted under 35 U.S.C. 154(b) by 77 days.

(21) Appl. No.: 12/674,150

(22) PCT Filed: Oct. 24, 2007

(86) PCT No.: PCT/CN2007/003034
§ 371 (c)(1),
(2), (4) Date: Apr. 8, 2010

(87) PCT Pub. No.: WO2009/023995
PCT Pub. Date: Feb. 26, 2009

(65) Prior Publication Data
US 2010/0248974 A1    Sep. 30, 2010

(30) Foreign Application Priority Data
Aug. 21, 2007    (CN) .......................... 2007 1 0018514

(51) Int. Cl.
*C07K 16/00*    (2006.01)
*G01N 31/00*    (2006.01)
(52) U.S. Cl. ......................................... 530/387.1; 436/4
(58) Field of Classification Search .................. None
See application file for complete search history.

(56) References Cited

FOREIGN PATENT DOCUMENTS
CN    1381461 A    11/2002
CN    1749268 A    3/2006

OTHER PUBLICATIONS

Ochrietor et al., "Retina-Specific Expression of 5A11/Basigin-2, a Member of the Immunoglobulin Gene Superfamily", Invest. Opth. & Vis. Sci., 2003, 44(9):4086-4096.*
McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Bao et al. (2004) Chin J. Cell. Mol Immunol., 20 (4), 437-440, Preparation of Human Fab Antibodies Against HAb18G by Guided Selection and Chain Shuffling Technique.
Xing et al. (2003) J Fourth Mil Med Univ, 24(12), 1057-1060, Prokaryotic Expression and Immunological Analysis of the Extracellular Domain of Hepatoma Associated Antigen HAb18G.
International Preliminary Report on Patentability for PCT/CN2007/003034.
English language translation of the Written Opinion of the International Searching Authority for PCT/CN2007/003034.
English Language Translation of the Abstract of CN 1381461 (A).
English Language Translation of the Abstract of CN 1749268 (A).

* cited by examiner

*Primary Examiner* — Suzanne M Noakes
(74) *Attorney, Agent, or Firm* — Leydig, Voit & Mayer, Ltd.

(57) ABSTRACT

A crystal, a preparation method and 3D structure of CD147 extracellular region are provided. Such 3D structure is useful in the determination of the active site of CD147 extracellular region by computer modeling or molecular docking method. The crystal and/or 3D structure are useful in a structure-based drug design and the selection of an antibody, a ligand or an interacting molecule of CD 147 extracellular region.

4 Claims, 5 Drawing Sheets

The organization of exons/introns in CD147 gene.

The crystal structure of the CD147 extracellular region

The complex of CD147 with its monoclonal antibody HAb18

The active binding sites of CD147

The amplification of the mutated fragment using high-fidelity polymerase HS-Primestar Sequencing result SDS-PAGE result Western-blot result

CRYSTAL STRUCTURE OF CD147 EXTRACELLULAR REGION AND USE THEREOF

CROSS REFERENCE TO RELATED APPLICATIONS

This application is a national phase filing under 35 U.S.C. §371 of PCT International Application PCT/CN2007/003034, filed Oct. 24, 2007, land published under PCT Article 21(2) in Chinese as WO 2009/023995 on Feb. 26, 2009. PCT/CN2007/003034 claimed priority from Chinese application No. 200710018514.X filed on Aug. 21, 2007. The entire contents of each of the prior applications are incorporated herein by reference.

FIELD OF THE INVENTION

The present invention relates to the crystal of CD147 extracellular region. The invention also relates to the steric structure of the crystal determined by X-ray diffraction and use thereof. More specifically, the invention relates to the use of the steric structure in the computational molecular modeling for determining the three dimensional structure and the active sites of a complex of CD147 extracellular region with its corresponding antibody HAb18, ligand or interacting molecule, and also to the use of the computational molecular modeling for identifying a protein, a peptide or a chemical, including an inhibitor, that can bind to CD147 extracellular region. The invention also relates to the identification of a CD147 inhibitor and the medical use thereof.

BACKGROUND OF THE INVENTION

CD147 is a widely expressed transmembrane glycoprotein, which has extensive physiological and pathogenic significance, and its primary functions comprise inducing the secretion of extracellular matrix metalloproteinase (EMMPRIN), interacting with CypA, mediating an inflammation, facilitating viral infection to host cell, etc. CD147 is closely related to embryo development, tumor invasion and metastasis, occurrence and development of inflammation, viral infection and proliferation, etc.

CD147 is widely expressed in hematopoietic and non-hematopoietic cells, such as hematopoietic cells, epithelial cells, endothelial cells and lymph cells. It is a transmembrane glycoprotein with a molecular weight of 50-60 KD. HAb18G/CD147, a highly glycosylated transmembrane protein, is a new member of the CD147 family and a novel liver cancer related membrane antigen. The anti-hepatoma monoclonal antibody HAb18 developed and purified by the inventors' lab was used to screen the cDNA library of human liver cancer cell, and a cDNA fragment (about 1.6 kb) corresponding to antigen HAb18G was cloned. After searching for the Genbank, the cDNA sequence of antigen HAb18G was found to be highly homologous to the base sequence of human CD147 molecule. The further analysis on the open reading frames showed that both proteins were encoded by the same gene. Based on this finding, we had proven the identity of these two molecules at protein level in different aspects. A further study showed that CD147 was an inducer for matrix metalloproteinases (MMPs) on tumor cell surface, and could stimulate the synthesis of matrix metalloproteinases through fibroblast. HAb18G/CD147 was assumed to possess the EMMPRIN function of CD147 molecule. In the previous study, using a tumor bearing mice model, we had proven that different doses of iodine-131 labeled metuximab monoclonal antibody injection led to different tumor suppression effects, and the tumor suppression of both medium and high doses was significantly different with the negative control group. Subsequently, a monoclonal antibody was labeled with $^{131}I$ to prepare $^{131}I$ labeled metuximab monoclonal antibody injection (LICARTIN), which could be used safely and effectively to treat primary liver cancer. Another clinical research showed that LICARTIN could be used as an anti-recurrence drug for liver cancer after the liver transplantation. After 1 year follow-up, the patients with liver transplantation in the treated group had decreased recurrence rate and increased survival rate comparing to the control group. The above studies demonstrated that CD147 molecule is a novel drug target for the treatment of tumors such as liver cancer.

We studied various tissue profiles of CD147 by using the antibody HAb18, demonstrating that the CD147 molecule was highly expressed (69.47%) in a cancer tissue originated from the epithelium, but not expressed in benign tumors, and expressed at a lower level in embryonic tissue and normal tissue (2.67% and 10.62%, respectively). It is a broad-spectrum cancer-specific tumor marker.

Human CD147 is a protein consisting of 269 amino acids with a molecular weight of up to about ~28 KD, and belongs to type I transmembrane protein family. From the cloned cDNA sequence, the mRNA of CD147 molecule was about 1.7 kb in length. No TATA box or CAAT box was found in the region associated with the transcription start site, but the transcription start site was located within CpG islands, especially in the region of nucleotide −247 to nucleotide +6. There is a non-coding region of about 115 nucleotides before the N-terminal start codon, and the coding region encodes 269 amino acids, in which 21 amino acids form a signal peptide, 185 amino acids in the middle form an extracellular domain, 24 amino acids of positions 206 to 229 form a transmembrane region, and 39 amino acids at C-terminus form an intracellular domain. 4 extracellular cysteines ($C^{41}$, $C^{87}$, $C^{126}$, $C^{185}$) form two disulfide bonds, constituting a typical IgSF hemispherical domain. In addition, there are three similar N-glycosylated asparagine sequences in extracellular region, and the glycosylation determines the MMP activating activity of CD147 molecule. The purified deglycosylated CD147 molecule cannot induce the activity of MMP, and antagonize the activity of natural CD147 molecule. Endo-F glycosidase digestion reduces the M.W. of CD147 molecule by about 30 KD, demonstrating that the glycosylation of CD147 molecule is primarily in the form of N-linked oligosaccharide.

The 24 amino acid residues in the transmembrane region are highly conserved in the CD147 molecules of human, mouse and chicken, indicating that the transmembrane fragment of CD147 molecule plays an important function and displays similar functions in various species [19]. There exists a charged glutamic acid residue in the transmembrane region, which is uncommon in other membrane protein molecules, indicating that CD147 molecule can associate with other transmembrane proteins [20]. The transmembrane region contains 3 leucine residues ($L^{206}$, $L^{213}$, $L^{220}$) and one phenylalanine residue, which occur once every 7 residues and is a typical leucine zipper structure. The charged residues and the leucine zipper structure in the transmembrane region are a potential protein interaction motif, which is very likely to mediate the participation of CD147 molecule in the generation of a signal transduction polypeptide chain or a component of a membrane transporter protein.

Currently there is no a comprehensive analysis for the cytoplasmic domain. Schlosshauer-B et al. had discovered the coexistence of CD147 and F-actin by double-labeling method, and found that the expression of CD147 on the membrane surface was related to microfilament proteins in cytoskeleton. Whether there is a phosphorylation site or how a signal is transduced is still unknown.

CD147 gene is encoded by 8 exons and is of 10.8 kb in total length. The nucleotide and protein sequences are shown in FIG. 1.

Exon1 (aa 1~23, 107 bp) and Exon2 (aa 2~75, 154 bp) are separated by Intron1 (about 6.5 kb) which is the biggest intron sequence in EMMPRIN gene. Intron2 is about 700 bp in length, and is the second biggest interfering sequence in said gene. Exon3 (aa 76~102, 83 bp) and Exon4 (aa 103~148, 138 bp) are separated by Intron3 (300 bp). Intron4 is about 650 bp in length. Exon5 (aa 149~240, 276 bp). Intron5 is about 550 bp in length. Exon6 (aa 241~249, 25 bp) is very short. Intron6 is about 250 bp in length. Exon7 (aa 250~269, 69 bp). Intron7 is about 300 bp in length. The last exon is Exon8 which is 736 bp in length. Exon1 encodes 5'-untranslated region (5'-UTR) and a signal peptide. Exon2 and Exon3 encode the first Ig1 domain, in which Exon2 encodes 52 codons which are about 66% of Ig1, and Exon3 encodes 27 codons which are about 34% of Ig1. Exon4 and Exon5 encode the second Ig domain, in which Exon4 encodes 46 codons which are about 45% of the domain. Exon5 is a "binding" exon, encoding the rest 55% of the Ig domain, the 24 amino acid residues in the transmembrane domain and a small part of the intracellular domain. Exon6 and Exon7 encode the intracellular domain, and Exon7 also encodes the stop codon and 5 nucleotides in 3'-UTR. Exon8 encodes the rest of 3'-UTR.

CD147 molecule is a potential adhesion molecule, the function of which is similar to those of N-CAM, I-CAM and other relevant IgSF subgroup molecules, involving in adhesion between cell and cell or cell and matrix. There were experiments to prove that CD147 molecule can form a protein complex with $\alpha 3\beta 1$ or $\alpha 6\beta 1$ of the Integrin family. The functions of the complex are still unknown, possibly relating to the adhesion between tumor cells and extracellular matrix, and between tumor cells and interstitial cells. There were other experiments demonstrating that some CD147 monoclonal antibodies can suppress the homotypic aggregation of estrogen dependent breast cancer cell lines MCF-7 and MDA-435, and the adhesion of MCF-7 cells to Type IV collagen, FN or LN. CD147 is a novel cell surface adhesion molecule which mediates cell adhesion. The expression of this kind of molecules and their functions in tumor is a focus in current tumor researches.

The biological function of a protein is largely dependent on its spatial structure, and the variety of protein structure conformations result in different biological functions. The relationship between the structure and the function of a protein is the basis for protein function prediction and protein design. A protein molecule can exhibit its specific biological activity only in its specific 3D spatial structure. A slight damage to the spatial structure probably leads to the reduction or even the loss of the biological activity of the protein. The specific structure allows the protein to bind to its specific ligand molecule, e.g. the binding of oxygen to hemoglobin or myoglobin, an enzyme to its substrate molecule, a hormone to its receptor, or an antibody to its antigen. If the code of a gene is known, scientists can deduce the amino acid sequence of the encoded protein, but cannot figure out the spatial structure of the protein. Along with the development of structural biology in recent years, using x-ray diffraction or NMR analysis, the steric structures of many proteins had been discovered by 3D structure and molecular design techniques. The understanding to the spatial structure of a protein would contribute to the determination of the protein's function. Also, if a protein is a target of a drug, combining the knowledge of the gene code and the structure information of the protein, a small molecule compound can be designed to inhibit the protein associated with a disease so as to treat the disease.

The illustration of CD147 protein structure would play an important role in the disease treatment or the diagnostic agent designing. Prior to the present invention, the structure of CD147 and the mechanism of CD147 to promote tumor progression, regulate tumor invasion or metastasis, mediate inflammation, or facilitate viral infection to host cell remain vague. Therefore, despite the knowledge about the general function and role of CD147 is known, the development of an agent for a disease (e.g. liver cancer) treatment or diagnosis is restricted due to the absence of the protein structural information.

Thus, there is a need to clarify the three dimensional structure of CD147 molecule and establish a corresponding model, which would contribute to the determination of the active sites of CD147 molecule interacting with a molecule such as an integrin, CypA, so as to utilize the structure and model for assisting the disease treatment, e.g. the structure-based drug design.

The term "steric structure of a protein" as used herein refers to three dimensional structure of a protein determined by amino acid sequence of the protein under certain conditions, namely the three dimensional structure formed by the folding of a protein with an amino acid sequence under certain conditions. X-ray diffraction or NMR can be used to determine the structure of a protein.

SUMMARY OF THE INVENTION

The present invention relates to the 3D coordinates and the 3D structure of the crystal of CD147 extracellular region with $P4_12_12$ space group in tetragonal crystal system and an amino acid sequence as shown in SEQ ID NO: 1, to the structural model and active interacting sites of a complex of CD147 extracellular region with its antibody HAb18 determined by said structure of CD147 extracellular region, and to use of the structures, models and active interacting sites. It is well known in the field of protein crystallography that whether a crystal with high resolution diffraction quality is a bottleneck for resolving protein structure. A stable disulfide bond is required in many proteins for the correct spatial structure. Without such disulfide bond, these proteins may be degraded or become inclusion bodies. The redox potential in *E. coli* is the main cause why a protein cannot fold correctly, and a disulfide bond can be formed in a protein only after the protein is transported to periplasmic space. We used Origami B (DE3) strain with double mutations in glutathione reductase (gor) and thioredoxin reductase (trxB), capable of increasing the formation of disulfide bonds in the cytoplasm, to generate more soluble and active protein. The study had also shown that even though the overall expression levels were similar, the level of the active protein from Origami (DE3) was 10 times higher than that from other stains. This is a possible reason why CD147 is mainly expressed in a form of inclusion body in the common-used BL21 (DE3), whereas in Origami (DE3) a soluble active protein can be obtained. Furthermore, before the present invention, the crystal of CD147 extracellular region with enough quality for 3D structure resolution was not obtained. Thus, before the present invention, the 3D structure of CD147 extracellular region had not been determined, let alone the active interacting sites of CD147 extracellular region. The present inventors clarify the 3D structure and the active interacting sites of CD147 extracellular region for the first time, and also provide a 3D model for the drug design to CD147.

Accordingly, one aim of this invention is to provide a crystal with enough quality for determining 3D structure of CD147 extracellular region. The invention also relates to a method for growing the crystal of CD147 extracellular region.

The second aim of this invention is to provide the 3D structure and model information of CD147 extracellular region.

The knowledge about the 3D structure of CD147 extracellular region provides a means (i.e. structure-based drug design) to design and produce an agent such as an antibody, a peptide, a protein, or a small molecule (including a chemical) for regulating tumorigenesis or tumor development and inhibiting tumor metastasis in an animal (including human). For example, using various computer softwares and models, the agent can be designed to inhibit the biological activities of CD147 molecule so as to inhibit tumor progression, the occurrence of inflammation, viral infection to host cell and so on.

Accordingly, the third aim of this invention is to provide a method comprising utilizing the obtained 3D structural information of CD147 extracellular region in combination with computer modeling to establish the structure of HAb18, an anti-CD147 monoclonal antibody, using such as computer simulation and molecular docking to determine the active sites of CD147 extracellular region, and designing an agent for disease treatment or diagnosis based on the amino acid sequences and the structures of the active sites.

Accordingly, the fourth aim of this invention is to utilize the 3D structure of CD147 extracellular region to design and produce an agent such as an antibody, a protein, a peptide, a small molecule (a chemical) and so on, capable of binding to CD147 extracellular region and inhibiting or stimulating the biological activities of CD147. The inhibitory or stimulatory agent can be determined according to the following: (a) providing the 3D structure of CD147 extracellular region, (b) designing an agent such as an antibody, a protein, a peptide or a small molecule (a chemical) etc, by using the structure (c) synthesizing the agent, and (d) evaluating the change of CD147 mediated embryo development, tumor invasion or metastasis, occurrence or development of inflammation, viral infection or proliferation, etc., caused by the synthesized agent.

DESCRIPTION OF THE DRAWINGS

FIG. 2A describes the space group of CD147 extracellular region, indicating one asymmetric single unit, wherein there are four molecules indicated by A, B, C and D chains, respectively, each molecule or each chain containing two Ig-like domains. FIG. 2B is an enlarged image of one chain, wherein two β-sheets in two different types of Ig-like domains are indicated (composed of different numbers and orientations of β-sheets, respectively). [1] Chothia C, Jones E Y. The molecular structure of cell adhesion molecules. *Annu Rev Biochem.* 1997; 66:823-62. [2] Vaughn D E, Bjorkman P J. The (Greek) key to structures of neural adhesion molecules. *Neuron.* 1996 February; 16(2):261-73.

DETAILED DESCRIPTION OF THE INVENTION

Figure 1:
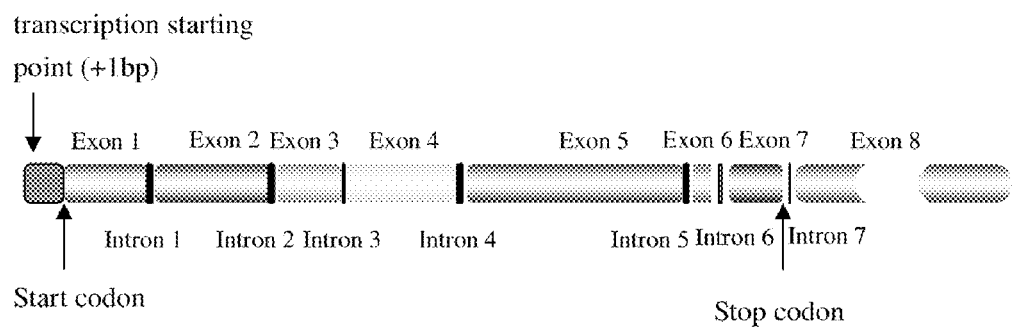
FIG. 1: The organization of exons/introns in CD147 gene.

The invention relates to the crystal of CD147 extracellular region and 3D structure thereof, to a model of the 3D structure, to a structure model and active interacting sites of a complex of CD147 extracellular region with its antibody HAb18 (determined by the structure of CD147 extracellular region), to a drug design method using the 3D structure, to an agent such as an antibody, a protein, a peptide, or a small molecule, identified by the method, to use of the agent in the disease treatment or diagnosis, and to use of the structure, model, and active interacting sites of CD147 extracellular region. It should be understood that the term as used herein such as "homolog", "fragment", "variant", "analogue" or "derivative" of the amino acid sequence of the crystal of the CD147 extracellular region, as mentioned in the appended claims, refers to a molecule obtained by substituting, varying, altering, replacing, deleting or adding one or more amino acid residues in the amino acid sequence of crystallized CD147 extracellular region of the invention, or the term may also refer to a molecule with a sequence within the amino acid sequence of crystallized CD147 extracellular region according to the invention.

The "variant" as used herein refers to the addition, deletion or replacement of an amino acid residue in the sequence of wildtype CD147 extracellular region or a fragment thereof. The variant of the amino acid sequence of the CD147 extracellular region according to the invention may comprise (1) the deletion of any one or more amino acid residues in the sequence, or (2) the replacement of any one or more amino acid residues in the sequence with one or more amino acid residues.

The term "homolog" as used herein refers to similarity in amino acid sequences, namely comparing the amino acid sequence of the crystal of CD147 extracellular region of the invention with another amino acid sequence, if at least 70% between the two amino acid sequences are identical, they are considered as homologs. The comparison method can be carried out manually or using a computer software such as CLUSTAL for homologous alignment.

The term "fragment" as used herein refers to any fragment of the amino acid sequence of the crystal of CD147 extracellular region provided in the invention, and this fragment is able to be crystallized.

The term "analogue" as used herein refers to a compound with a similar amino acid sequence to that of the crystal of CD147 extracellular region provided in the invention, and the similar amino acid sequence contains an amino acid replacement or deletion that does not affect the crystallizability of the amino acid sequence.

The term "derivative" as used herein refers to an amino acid sequence obtained by chemical modification in the amino acid sequence of the crystal of CD147 extracellular region of the invention, such as the substitution of hydrogen in alkyl group, acyl group or amino group, etc.

The crystal of CD147 extracellular region according to the invention refers to not only the naturally occurring crystal of CD147 molecule or the crystal obtained by crystallization of wildtype CD147, but also the crystal of a mutant of wildtype CD147 that have same 3D structure as wildtype CD147 molecule. A mutant of wildtype CD147 molecule may be: substitution of at least one amino acid in wildtype CD147 molecule, addition/deletion of an amino acid in a peptide chain of wildtype CD147 molecule or addition/deletion of an amino acid at the N-or C-terminus of a peptide chain of wildtype CD147 molecule.

In one embodiment, the crystal of CD147 extracellular region has a cubic crystal cell with following crystal lattice constants: $a=126.481$ Å$\pm 0.5\%$, $b=126.481$ Å$\pm 0.5\%$, $c=169.926$ Å$\pm 0.5\%$, $\alpha=\beta=\gamma=90°$. Its amino acid sequence is set forth in SEQ ID NO: 1. Moreover, the invention provides a method for preparing the crystal of CD147 extracellular region, comprising the following steps: cloning the gene sequence for CD147 extracellular region into the prokaryotic expression system pET21a(+), expressing it in Origami B (DE3) strain, purifying the CD147 extracellular region protein, preparing a solution of the CD147 extracellular region protein in 5-20 mg/ml and a reservoir solution of 0.5M ammonium sulfate, 0.1M sodium citrate and 1.0M lithium sulfate, pH 5.6, mixing the solution of the CD147 extracellular region protein with the reservoir solution, and standing the mixture solution for a period of time until a crystal of CD147 extracellular region forms and grows to the predefined size or even bigger.

In another embodiment, X-ray diffraction is adopted to determine the 3D structure of the crystal of CD147 extracellular region, comprising: resolving the structure by using single wavelength anomalous dispersion (SAD). One set of diffraction data for the crystal of the natural protein (2.8 Å resolution) and one set of diffraction data for the crystal of the seleno-substituted protein (3.1 Å resolution) are collected from each of BL17A and NW12 beamlines of the synchrotron radiation light source (Photon Factory, Japan), and the software package HKL2000 is used to process the data. Firstly the data of the crystal of seleno-substituted protein is used to obtain phase information and initial structure model, and then the diffraction data of the crystal of the natural protein is used for structure determination and refinement.

A suitable computer modeling program such as WAM (Web Antibody Modeling) can be used in simulating calculation of a 3D structure of CD147 extracellular region that can substantially satisfy the definition of claim 1. This simulating calculation requires some information like: (1) the amino acid sequence of CD147 extracellular region; (2) the amino acid sequences of the parts related to 3D structure; and (3) specific 3D structural information. The 3D structure of other forms of CD147 extracellular regions (a mutant, a fragment, a derivative, a variant, an analogue or a homolog of CD147 extracellular region) essentially matching with the 3D structure of CD147 extracellular region according to the present invention can also be calculated using a molecular replacement method, which is described in detail below.

Table 1 gives a 3D structure of CD147 extracellular region which is suitable for simulating or calculating the 3D structure of another CD147 extracellular region. According to the invention, using the above 3D structure, persons skilled in the art can simulate or calculate the 3D structure of a mutant, a fragment, a derivative, a variant, an analogue or a homolog of CD147 extracellular region that has a similar amino acid sequence as CD147 extracellular region described in the invention. These techniques are based on the information obtained from the analysis of the crystal of CD147 extracellular region. Therefore, the determination of the 3D structure of the crystal of CD147 extracellular region enables one to apply conventional techniques in the art to derivatize the 3D structure or model for a mutant, a fragment, a derivative, a variant, an analogue or a homolog of CD147 extracellular region. The derivatization of any structure of a mutant, a fragment, a derivative, a variant, an analogue or a homolog of CD147 extracellular region can even be accomplished in the absence of the structural data in respect of the crystal thereof. Moreover, using the information obtained from the crystal of CD147 extracellular region in the invention, it is possible to optimize the simulation of the 3D structure of a newly mutant, fragment, derivative, variant, analogue or homolog of CD147 extracellular region when working on these crystal structures. One advantage of the invention is that, in the absence of other crystal structural data of a mutant, a fragment, a derivative, a variant, an analogue or a homolog of CD147 extracellular region, given the difference between the amino acid sequences between the mutant, the fragment, the derivative, the variant, the analogue or the homolog of CD147 extracellular region and the CD147 extracellular region according to the present invention, it is possible to simulate the 3D structure of the mutant, the fragment, the derivative, the variant, the analogue or the homolog of CD147 extracellular region. In addition, the invention makes the determination of the active sites of CD147 extracellular region for an antibody, an integrin, CypA or another interacting molecule, the structure-based drug design and the drug screening realizable. An antibody, a protein, a peptide or a small molecule (a chemical) thus designed and screened out can effectively affect the activity of CD147 molecule.

The crystal model of CD147 extracellular region according to the invention can contribute to the selection of an antibody, a ligand or another interacting molecule of CD147, and the determination of the active interacting sites, especially the selection of an inhibitory molecule such as an antibody, a peptide, a protein or a chemical molecule. For example, a method for co-crystallization of CD147 extracellular region with an antibody, a ligand or another interacting molecule can be used; an antibody, a ligand or another interacting molecule can be dissolved in the crystal of CD147 extracellular region; a computer can be used to dock the model of the crystal of CD147 extracellular region with the model of the crystal of an antibody, a ligand or another interacting molecule so as to screen a ligand for CD147, especially an inhibitory molecule of CD147; or a computer can be used to design and screen out a reagent, an antagonist or a drug that can bind to the active binding sites of the crystal of CD147 extracellular region. Before the discovery of the 3D structure of the invention, no information can be used for the structural development of a diagnostic or therapeutic compound based on CD147 extracellular region structure. Up to now it is impossible to perform this design only based on linear amino acid sequence. Structure-based drug design refers to using computational simulation to predict the interaction of a protein conformation with an antibody, a peptide, a polypeptide, a protein or a chemical substance. Generally, for a protein that can effectively interact with a therapeutic antibody, a peptide, a protein or a chemical molecule, the 3D structure of the therapeutic compound is supposed to have a compatible conformation to ensure the binding. The knowledge of the protein 3D structure enables persons skilled in the art to design a diagnostic or therapeutic antibody, peptide, protein or chemical molecule with similar compatible conformation. For example, the information of the binding sites of CD147 extracellular region to its antibody HAb18 enables persons skilled in the art to design an antibody, a peptide, a protein or a chemical that can bind to, and inhibit the biological activities of CD147.

The determination of the 3D structure of CD147 extracellular region provides the important information for the determination of possible active sites in CD147 extracellular region. The structural information is helpful for designing an inhibitor of CD147 molecule for the active sites of the molecule. For example, the computer technique can be used to identify a ligand that can bind to an active site or design a drug, or X-ray crystal diffraction analysis can be used to identify and locate the binding sites of a ligand.

Greer et al. used repeated sequences of computer model, structure of protein-ligand complex and X-ray diffraction method to design an inhibitor of thymine nucleotide. Therefore, an inhibitor of CD147 molecule can also be designed as such. For example, using the 3D structure of CD147 extracellular region according to the invention, by a computer modeling, we can design an agent such as an antibody, a protein, a peptide or a small molecule capable of binding to the functional active sites or other sites in the 3D structure according to the invention, synthesize the agent, form a complex of the agent with CD147, and then use X-ray crystal diffraction to analyze the complex to identify the actual binding sites. Based on the result of X-ray crystal diffraction, the structure and/or functional groups of a ligand can be adjusted accordingly until an optimized agent molecule is obtained.

Moreover, based on the result of the 3D structure of CD147 extracellular region, many computer softwares can be used in inferential drug design so as to design an inhibitor of CD147 molecule. For example, automated ligand-receptor docking softwares can be used (Jones et al. in Current Opinion in Biotechnology, Vol. 6, (1995), 652-656). Detailed and precise 3D structural information of CD147 extracellular region is necessary in the method.

The drug design by linking fragments also requires precise 3D structural information of the target receptor. This method is to determine the sites of several ligands for binding to the target molecule, and then construct a molecular scaffold linked to a ligand. Thus, ligands are linked to form a potential directing complex, and then the iterative technique is used to confirm. The inhibitor of CD147 can also be designed as such.

In the above described methods of structure-based drug design, it is necessary to determine an agent that can interact with a target biological molecule first. Sometimes, this agent can be found in literature. However, most of the inhibitors for a target molecule are unknown, or a novel inhibitor for a target molecule is desired. For this, one need first search a database (e.g. the Cambridge Structural Database) for compounds that can interact with active sites or sites of the target molecule. Where the structure of a target molecule is unknown, the searching is generally based on a pharmacokinetic characteristic, such as metabolic stability or toxicity. However, the determination of the structure of CD147 extracellular region makes it possible to screen based on the structure and characteristic of the active sites of the molecule. The screening can be based on whether a potential inhibitor can form an effective 3D Pharmacophore with CD147 extracellular region.

In one embodiment of the invention a method comprising using computer-assisted 3D modeling, molecular docking technique selection and the determination of an antibody, a ligand or another interacting molecule of CD147 extracellular region is provided, comprising: (1) providing a protein structure comprising a 3D structure or model of the CD147 extracellular region according to the invention, and predicting the structure of a possible antibody, ligand or interacting molecule by utilizing computer 3D modeling; (2) docking the 3D structures of CD147 extracellular region and the antibody, the ligand or the interacting molecule; (3) evaluating whether the 3D structure of the antibody, the ligand or the interacting molecule can bind to the 3D structure of the active sites of CD147 extracellular region, and further analyzing comprising (4) analyzing the biological activities of the antibody, ligand or the interacting molecule of CD147 extracellular region for CD147; (5) whether the antibody, ligand or the interacting molecule of CD147 extracellular region can regulate the biological functions of CD147.

In another embodiment of the invention, a computer-assisted method for structure-based drug design is provided, comprising: (1) providing a protein structure comprising a 3D structure or model of the CD147 extracellular region according to the invention; (2) designing an antibody, a peptide, a protein or a compound by using the 3D structure or model; (3) synthesizing the antibody, the peptide, the protein or the compound.

The ligand, interacting molecule or inhibitory antibody, peptide, protein, or chemical according to the invention can be identified using various methods known to persons skilled in the art, e.g. a ligand, an interacting molecule or an antibody, a peptide, a protein, or a chemical can be bound to or interacted with CD147 extracellular region protein, determined in CD147 protein in solution or on cell, and screened and identified by using such as an immunoassay like enzyme-linked immunosorbent assay (ELISA) or radioimmunoassay (RIA), a binding assay like Biacore, yeast two hybrid, phage peptide library or an antibody library.

The following examples are used to illustrate the invention in more details. These examples are provided to explain but not limit the invention.

EXAMPLE 1

Generation of the Crystal of CD147 Extracellular Region and Resolution of the Structure of the Crystal 1. Cloning the gene sequence for CD147 extracellular region into the prokaryotic expression system pET21a(+), expressing it in Origami B (DE3) strain, and purifying CD147 extracellular region.
2. The CD147 extracellular region has the sequence as shown in SEQ ID NO: 1.
3. Crystallizing CD147 extracellular region.
4. Resolving the structure of the crystal.

Single wavelength anomalous dispersion (SAD) is used to resolve the structure. One set of diffraction data for the crystal of a natural protein (2.8 Å resolution) and one set for the crystal of a seleno-substituted protein (3.1 Å resolution) are collected from each of BL17A and NW12 beamlines of the synchrotron radiation light source (Photon Factory, Japan), and the software package HKL2000 is used to process the obtained data. First the data of the crystal of the seleno-substituted protein are used to get phase information and initial structure model, and then the diffraction data of the crystal of the natural protein are used for structure determination and refinement. The space group of the crystal is $P4_12_12$, and there are four molecules in one asymmetric unit, the crystal lattice parameters being: a=126.481 Å, b=126.481 Å, c=169.926 Å, α=90°, β=90°, γ=90°.

The Detailed Steps

1. Preparation and Purification of CD147 Extracellular Region
   1) Vector: pET21a(+), NdeI/XhoI cloning sites
   2) Host cell: Origami B (DE3)
   3) Expression: 1 mM IPTG induction, 20° C., overnight Purification
1) HiTrap Q Hp, 20 mM Tris pH 8.0 w/wo 1M NaCl
2) Mono Q HR 10/10, 20 mM Tris pH 8.0 w/wo 1M NaCl
3) HiLoad 16/60 Superdex 75 prep grade, 20 mM Tris pH 8.0, 150 mM NaCl 2. Protein Crystallization Hanging-Drop Vapor Diffusion Procedure
1) Protein concentration: 5-20 mg/ml
2) Reservoir solution: 0.5M ammonium sulfate, 0.1M sodium citrate and 1.0M lithium sulfate, pH 5.6.
3) Growth period: 3-4 weeks, 4° C.

3. Structure Determination

X-Ray Diffraction and Data Collection

Figure 2:
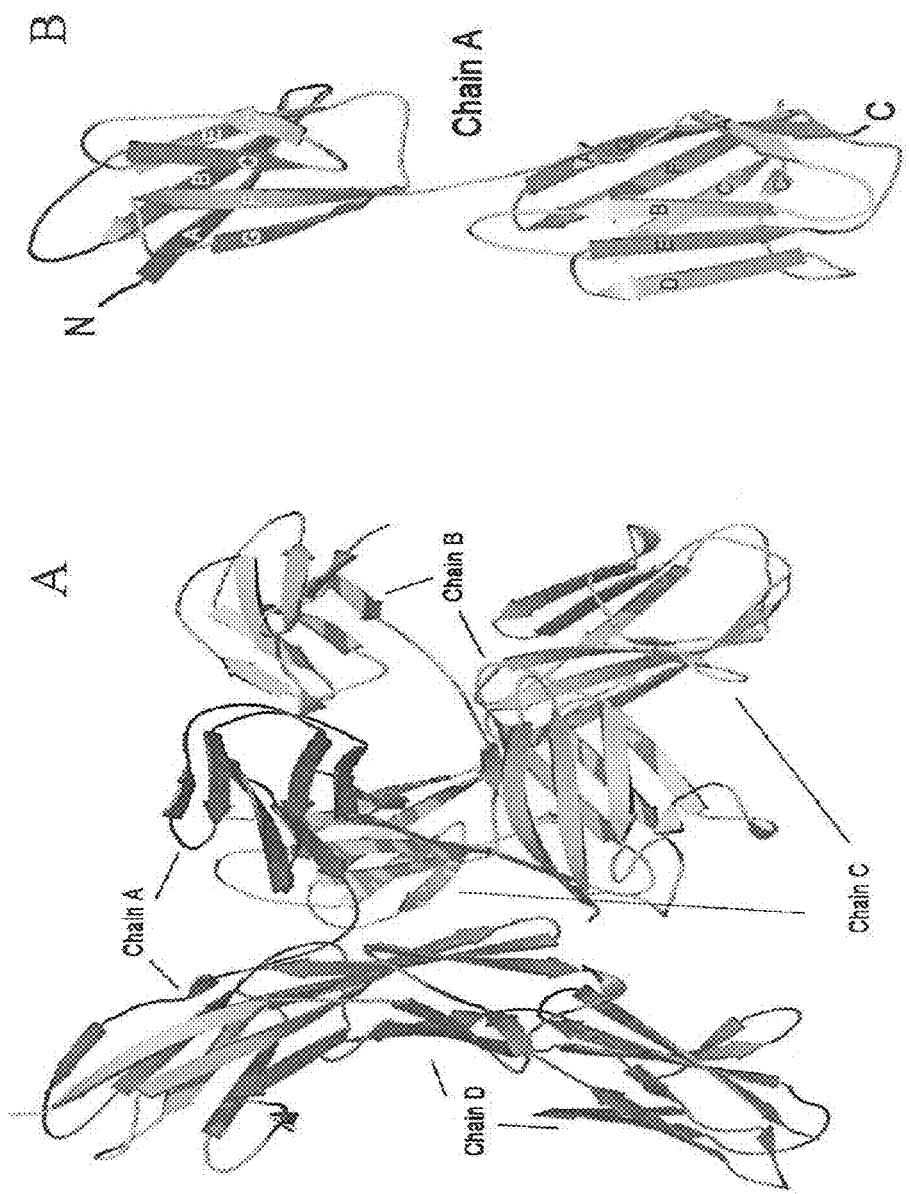
FIG. 2: The crystal structure of the CD147 extracellular region.

Single wavelength anomalous dispersion (SAD) was used to resolve the structure. One set of diffraction data for the crystal of a natural protein (2.8 Å resolution) and one set for the crystal of a seleno-substituted protein (3.1 Å resolution) were collected from each of BL17A and NW12 beamlines of the synchrotron radiation light source (Photon Factory, Japan), and the software package HKL2000 was used to process the obtained data. First the data of the crystal of the seleno-substituted protein were used to obtain phase information and initial structure model, and then the diffraction data of the crystal of the natural protein were used for structure determination and refinement (Table 1, FIG. 2).

EXAMPLE 2

CD147 extracellular region and antibody HAab18 modeling and docking, the determination of the active sites of CD147 extracellular region, and experimental confirmation.

1. The structure of the complex formed by the CD147 extracellular region and its antibody had following characteristics: there were 3 peptide chains in the molecular docking model of CD147 extracellular region and HAb18 molecule, namely the CD147 extracellular region and the variable domains of the light and heavy chains of HAb18; 6176 atoms were present, and 6635 covalent bonds were formed; and the docking energies were assessed as: binding energy=101.21, docking energy=29.05, intermolecular energy=30.54, torsional energy=70.67, internal energy=−1.49.

2. The active structural sites of the CD147 extracellular region had following characteristics: the active sites of CD147 extracellular region were located in the membrane-distal loop region of C2-set domain at N-terminus of the protein, and the amino acid residues involving in epitope were: Glu28, Thr30, Asp44, Ala45, Leu46, Pro47, Gly48, Lys50 and Glu52, wherein Glu28, Thr30 and Asp44 were more important, namely they formed hydrogen bonds with CDRH3, CDRH2 and CDRL3 in HAb18.

3. Glu28, Thr30 and Asp44 of the CD147 extracellular region were mutated, and by Western-blot, the three amino acids were proven to be involved in the site of CD147 for binding to anti-CD147 monoclonal antibody HAb18, and also played important role in the site.

The Detailed Steps

1. WAM (Web Antibody Modeling) was used to perform homology modeling for HAb18, and G-factors overall value is −0.21 by using Procheck V3.4. DeepView/Swiss-pdb-Viewer V3.7 was used to perform Energy Minisation and Compute Energy (GROMOS96 43B1 parameters set) for the HAb18 homology modeling result, and the total energy was determined as −5888.806 KJ/mol.

2. DeepView/Swiss-pdbViewer V3.7 was used to revise the spatial structure of HAb18/CD147 complex, add polar and nonpolar hydrogens, and correct the charge numbers of atoms.

Figure 3:
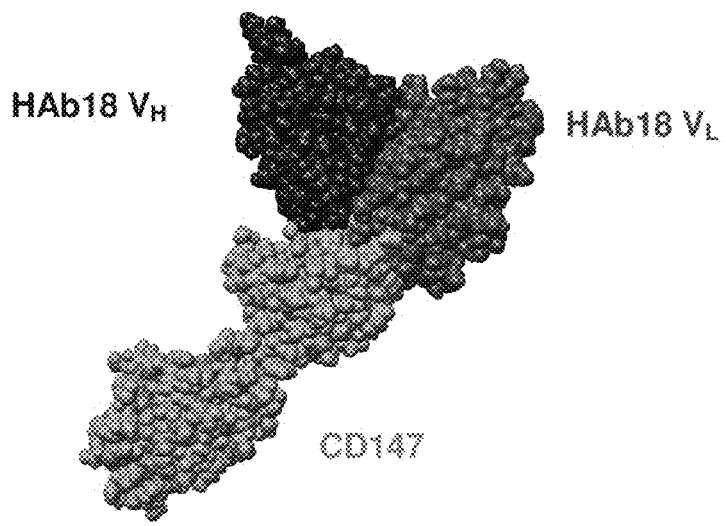
FIG. 3: The complex of CD147 with its monoclonal antibody HAb18.

3. AutoDock V3.0.5 was used for docking HAb18 with CD147 extracellular section, and the direction for molecular docking was roughly determined. Based on this, the precision was increased and a refine docking was performed. Then the docking model (FIG. 3) with most rational energy evaluation was determined. DeepView/Swiss-pdbViewer V3.7 was used to perform Energy Minisation and Compute Energy (GROMOS96 43B1 parameters set) for the docking result, and the total energy of the complex formed between HAb18 and CD147 extracellular region was −15383.64 KJ/mol.

Figure 4:
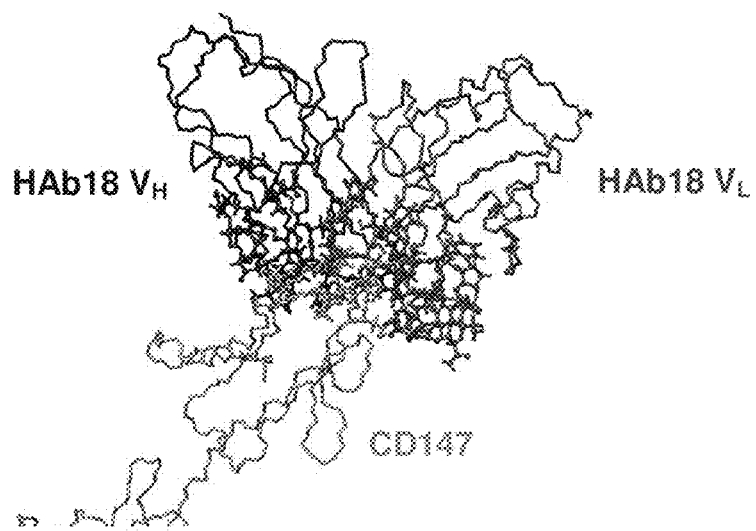
FIG. 4: The active binding sites of CD147.
Figure 5:
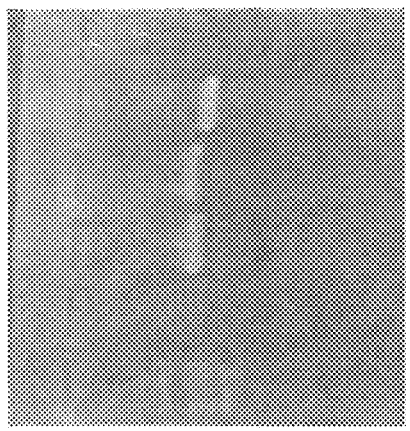
FIG. 5: The amplification of the mutated fragment using high-fidelity polymerase HS-Primestar. From left to right: Marker2000; Blank; P2 (Primers M5&F3); Full-length CD147 (Primers F5&F3); P1 (Primers F5&M3).
Figure 6:
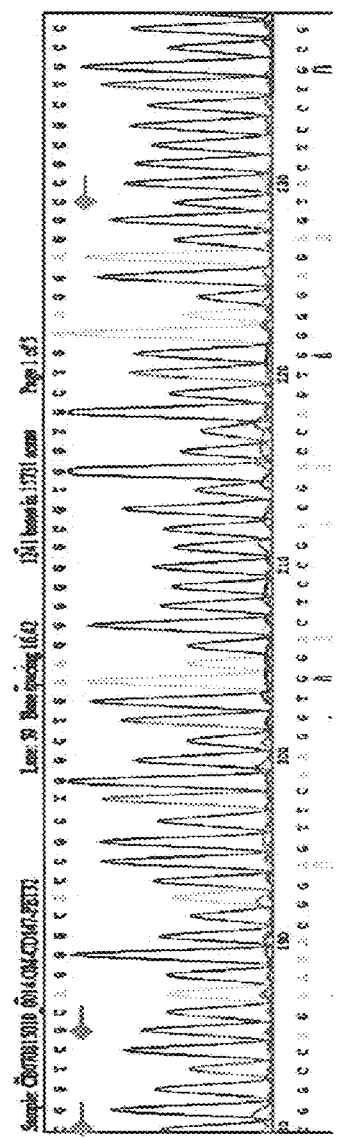
FIG. 6: Sequencing result.
Figure 7:
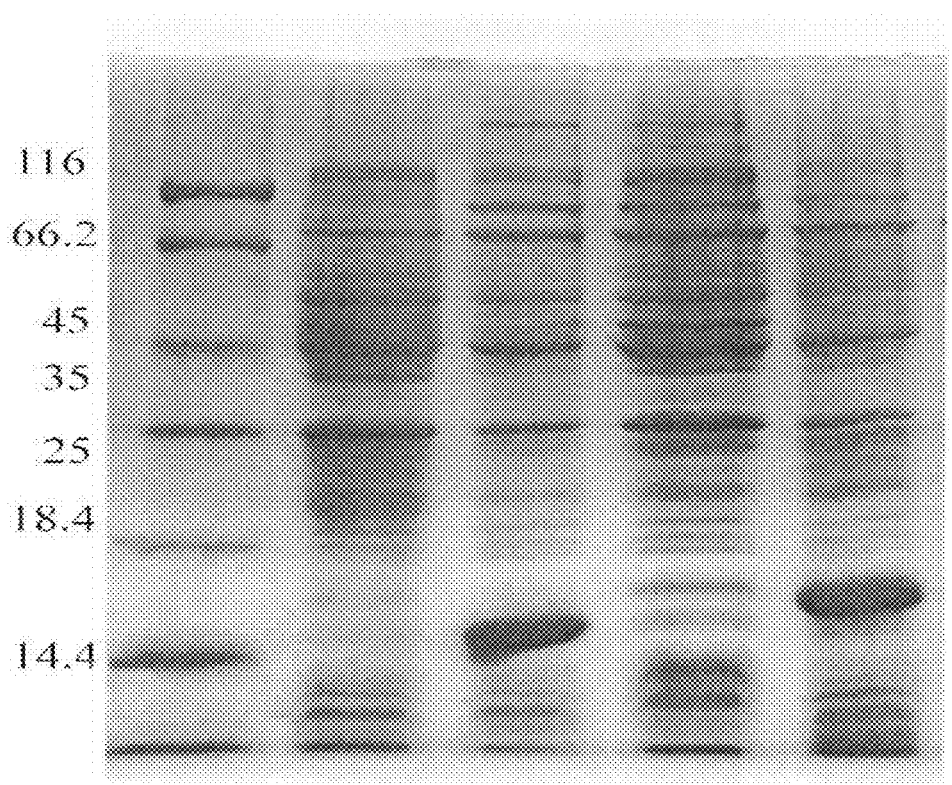
FIG. 7: SDS-PAGE result. From left to right: Marker; uninduced CD147; induced CD147; uninduced Mut-147; induced Mut-147.
Figure 8:
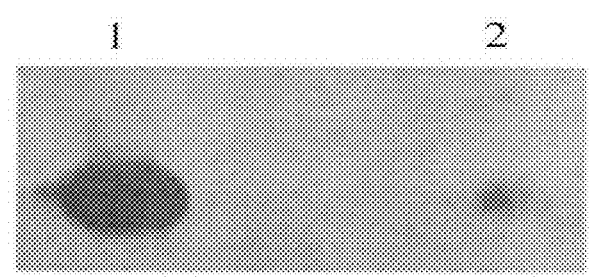
FIG. 8: Western blot result. From left to right: Induced CD147; Induced Mut-147. It can be seen that the affinity of the mutated Mut-147 to the anti-CD147 monoclonal antibody HAb18 is clearly decreased, demonstrating that the three amino acids E28, T30 and D44 are important in the binding of CD147 to the monoclonal antibody HAb18.

4. IFR Contact of STING MILLENNIUM was used to analyze the docking model to determine the amino acid residue sites for interaction (FIG. 4).

5. Experimental Confirmation for the Active Sites.

After several blinding docking, the model with the lowest docking energy was then performed for energy minimization and molecular dynamics using Insight II 2005, to obtain an optimized docking model, which showed that the interaction between the antibody and the antigen was mainly in two peptide chains ($A_{26}TEVTG_{31}$ and $D_{44}ALPGQ_{49}$), wherein E28, T30 and D44 were more important, namely they formed hydrogen bonds with CDRH3, CDRH2 and CDRL3 in HAb18. Therefore the mutations in the overall sequence should be E49A, T51A and D65A. As for the bases, the mutations were: 1 GAG- - -GCG; 2 ACA- - -GCA; 3 GAC- - -GCC. Thus, the primers were designed as follow:

```
FULL-147 5'
                                         (SEQ ID NO: 2)
5'CTGAATTCCATATGGCTGCCGGCACAGTCTTC3'

FULL-147 3'
                                         (SEQ ID NO: 3)
5'GCGCTCGAG GTGGCTGCGCACGCGGAGCG3'

Mut-147 3'
                                         (SEQ ID NO: 4)
5' CACGCCCCCCTTCAGCCAGCGGTGCCCTGCGACCGCTGT 3'

Mut-147 5'
                                         (SEQ ID NO: 5)
5'CTGGCTGAAGGGGGCGTGGTGCTGAAGGAGGCCGCG3'
```

By PCR, P1 fragment was obtained using primers FULL-147 5' and Mut-147 3', and P2 fragment was obtained using primers Mut-147 5' and FULL-147 3'. The products P1+P2 were annealed, and the primers FULL-147 5' and FULL-147 3' were used again to generate a full-length mutated Mut-147 for the prokaryotic expression of the extracellular region. The expressed product was finally identified with SDS-PAGE and Western-blot (FIG. 5-8).

It can be seen that, the affinity of the mutated Mut-147 with anti-CD147 monoclonal antibody HAb18 is clearly decreased, demonstrating that the three amino acids E28, T30 and D44 play important role in the interaction between CD147 and the monoclonal antibody HAb18.

Result:

TABLE 1

CD147 extracellular region crystal diffraction data

|  | Protein crystal | Seleno-substituted Protein Crystal |
|---|---|---|
| Data collection | | |
| Space group | $P4_12_12$ | $P4_12_12$ |
| Cell dimensions | | |
| a, b, c (Å) | 126.481, 126.481, 169.926 | 125.141, 125.141, 169.660 |
| α, β, γ (°) | 90, 90, 90 | 90, 90, 90 |
| Resolution (Å) | 50 – 2.80 (2.90 – 2.80) [a] | 50 – 3.10 (3.21 – 3.10) |
| $R_{sym}$ or $R_{merge}$ [b] | 0.106 (0.586) | 0.114 (0.697) |
| I/σ I | 18.4 (2.2) | 38.1 (5.8) |
| Completeness (%) | 99.4 (100) | 99.7 (100%) |
| Redundancy | 7.3 (7.4) | 28.5 (29.6) |
| Refinement | | |
| Resolution (Å) | 50 – 2.8 | |
| No. reflections | 32613 | |
| $R_{work}$ / $R_{free}$ [c] | 0.255/0.296 | |
| No. atoms | 5527 | |
| Protein | 5527 | |
| B-factors | 30.603 | |
| Main chains | 29.279 | |
| Side chains | 32.049 | |
| R.m.s deviations | | |
| Bond lengths (Å) | 0.010 | |
| Bond angles (°) | 1.397 | |
| Ramachandran statistics | | |
| Most favoured regions (%) | 82.7 | |
| Additionally allowed regions (%) | 15.2 | |
| Generously allowed regions (%) | 1.8 | |
| Disallowed regions (%) | 0.3 | |

[a] Numbers in parentheses refer to the highest resolution shell $$^b R_{sym}(R_{merge}) = \sum_{hkl}\sum_{i} |I_i(hkl)_i - \langle I(hkl) \rangle| \bigg/ \sum_{hkl}\sum_{i} I_i(hkl)$$

$$^c R = \sum |F_o| - |F_c| \bigg/ \sum |F_o|$$

The invention claimed is:

1. A crystal of CD147 extracellular region, wherein the crystal has P4$_1$2$_1$2 space group in a tetragonal crystal system and comprises amino acid sequence SEQ ID NO: 1, and is represented by a model which has a three-dimensional (3D) structure as in table 1, wherein the crystal has the following crystal lattice constants: a=126.481 Å±0.5%, b=126.481 Å±0.5%, c=169.926 Å±0.5%, α=β=γ=90°, and there are four molecules in one asymmetric unit wherein the molecular weight of one molecule is about 20±0.5KD, and the solvent content of said crystal is about 70±1%.

2. The crystal of CD147 extracellular region of claim 1, wherein the structure of the crystal has 3D spatial structural characteristics of the crystal of CD147 extracellular region, and the structure of the crystal of CD147 extracellular region shows that the CD147 extracellular region contains two Ig-like domains, wherein the N-terminal domain is Ig C2-set, whereas the C-terminal domain close to the cell membrane belongs to Ig 1 set.

3. The crystal of CD147 extracellular region of claim 1, wherein the sequence of CD147 extracellular region is of human origin.

4. The crystal of CD147 extracellular region of claim 1, wherein the crystal of CD147 protein is prepared by the following method: cloning the gene sequence for CD147 extracellular region into the prokaryotic expression system pET21a(+), expressing and purifying CD147 extracellular region; providing a solution of CD147 extracellular region at 5-20 mg/ml. preparing a pool solution of 0.5M ammonium sulfate, 0.1 M sodium citrate and 1.0 M lithium sulfate, pH 5.6; mixing the solution of CD147 extracellular region with the pool solution; standing the mixture solution for a period of time until a crystal of CD147 extracellular region grows to the predefined size or larger.

* * * * *

SEQUENCE LISTING

<160> NUMBER OF SEQ ID NOS: 5

<210> SEQ ID NO 1
<211> LENGTH: 184
<212> TYPE: PRT
<213> ORGANISM: Homo sapiens

<400> SEQUENCE: 1

```
Ala Ala Gly Thr Val Phe Thr Thr Val Glu Asp Leu Gly Ser Lys Ile
1               5                   10                  15

Leu Leu Thr Cys Ser Leu Asn Asp Ser Ala Thr Glu Val Thr Gly His
            20                  25                  30

Arg Trp Leu Lys Gly Gly Val Val Leu Lys Glu Asp Ala Leu Pro Gly
        35                  40                  45

Gln Lys Thr Glu Phe Lys Val Asp Ser Asp Asp Gln Trp Gly Glu Tyr
    50                  55                  60

Ser Cys Val Glu Leu Pro Glu Pro Met Gly Thr Ala Asn Ile Gln Leu
65                  70                  75                  80

His Gly Pro Pro Arg Val Lys Ala Val Lys Ser Ser Glu His Ile Asn
                85                  90                  95

Glu Gly Glu Thr Ala Met Leu Val Cys Lys Ser Glu Ser Val Pro Pro
            100                 105                 110

Val Ile Asp Trp Ala Trp Tyr Lys Ile Thr Asp Ser Glu Asp Lys Ala
        115                 120                 125

Leu Met Asn Gly Ser Glu Ser Arg Phe Phe Val Ser Ser Ser Gln Gly
    130                 135                 140

Arg Ser Glu Leu His Ile Glu Asn Leu Asn Met Glu Ala Asp Pro Gly
145                 150                 155                 160

Gln Tyr Arg Cys Asn Gly Thr Ser Ser Lys Gly Ser Asp Gln Ala Ile
                165                 170                 175
```

```
Ile Thr Leu Arg Val Arg Ser His
            180

<210> SEQ ID NO 2
<211> LENGTH: 32
<212> TYPE: DNA
<213> ORGANISM: Artificial
<220> FEATURE:
<223> OTHER INFORMATION: primer

<400> SEQUENCE: 2
ctgaattcca tatggctgcc ggcacagtct tc                                    32

<210> SEQ ID NO 3
<211> LENGTH: 29
<212> TYPE: DNA
<213> ORGANISM: Artificial
<220> FEATURE:
<223> OTHER INFORMATION: primer

<400> SEQUENCE: 3
gcgctcgagg tggctgcgca cgcggagcg                                        29

<210> SEQ ID NO 4
<211> LENGTH: 39
<212> TYPE: DNA
<213> ORGANISM: Artificial
<220> FEATURE:
<223> OTHER INFORMATION: primer

<400> SEQUENCE: 4 cacgccccc ttcagccagc ggtgccctgc gaccgctgt                              39

<210> SEQ ID NO 5
<211> LENGTH: 37
<212> TYPE: DNA
<213> ORGANISM: Artificial
<220> FEATURE:
<223> OTHER INFORMATION: primer

<400> SEQUENCE: 5
ctggctgaag gggggcgtgg tgctgaagga ggccgcg                               37
```